United States Patent
Pallone et al.

(10) Patent No.: US 9,532,029 B2
(45) Date of Patent: Dec. 27, 2016

(54) 3D SCANNING LASER SYSTEMS AND METHODS FOR DETERMINING SURFACE GEOMETRY OF AN IMMERSED OBJECT IN A TRANSPARENT CYLINDRICAL GLASS TANK

(71) Applicant: The Trustees of Dartmouth College, Hanover, NH (US)

(72) Inventors: Matthew Pallone, White River Junction, VT (US); Paul M. Meaney, Hanover, NH (US); Keith D. Paulsen, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 672 days.

(21) Appl. No.: 13/726,050

(22) Filed: Dec. 22, 2012

(65) Prior Publication Data

US 2013/0135450 A1    May 30, 2013

Related U.S. Application Data

(63) Continuation of application No. PCT/US2011/041448, filed on Jun. 22, 2011.
(Continued)

(51) Int. Cl.
*H04N 13/02* (2006.01)
*A61B 5/00* (2006.01)
(Continued)

(52) U.S. Cl.
CPC ......... *H04N 13/0221* (2013.01); *A61B 5/0091* (2013.01); *A61B 5/0507* (2013.01);
(Continued)

(58) Field of Classification Search
None
See application file for complete search history.

(56) References Cited

U.S. PATENT DOCUMENTS 4,174,634 A * 11/1979 Dory ...................... G01H 9/002
                                                                         73/606
5,773,721 A *  6/1998 Bashyam ............... G01B 17/06
                                                                        600/459
(Continued)

FOREIGN PATENT DOCUMENTS

WO    2007029038 A1    3/2007

OTHER PUBLICATIONS

International Search Report and Written Opinion issued in related PCT Patent Application PCT/US2011/041448, dated Feb. 28, 2012, 11 pages.
(Continued)

*Primary Examiner* — Frederick Bailey
(74) *Attorney, Agent, or Firm* — Lathrop & Gage LLP

(57) ABSTRACT

Systems and methods generate a 3D model of a surface of an object immersed in a transparent liquid within a stationary cylindrical transparent tank. First and second laser line projectors and a camera are rotated around a central axis of the cylindrical tank. The first and second laser line projectors each generate a laser line perpendicular to a plane or rotation and aligned with the center of rotation. The camera images the object. An image from the camera is captured at each of several angular positions of the camera relative to a reference position of the stationary cylindrical tank. The captured images are processed to determine, for each laser line within each image, a plurality of 3D positions where the laser line is incident upon a surface of the object. In embodiments, images are corrected with ray tracing or image warping and registration functions.

16 Claims, 9 Drawing Sheets

Related U.S. Application Data

(60) Provisional application No. 61/357,785, filed on Jun. 23, 2010.

(51) Int. Cl.

| | | |
|---|---|---|
| *A61B 5/05* | (2006.01) | |
| *A61B 5/107* | (2006.01) | |
| *G06T 15/06* | (2011.01) | |
| *G06T 17/00* | (2006.01) | |
| *G06T 1/00* | (2006.01) | |
| *G06T 5/00* | (2006.01) | |
| *G06T 7/00* | (2006.01) | |

(52) U.S. Cl.
CPC .......... *A61B 5/1077* (2013.01); *A61B 5/4312* (2013.01); *G06T 1/0007* (2013.01); *G06T 5/006* (2013.01); *G06T 7/0057* (2013.01); *G06T 15/06* (2013.01); *G06T 17/00* (2013.01); *G06T 2210/41* (2013.01)

(56) References Cited

U.S. PATENT DOCUMENTS

| | | | | |
|---|---|---|---|---|
| 6,064,423 | A * | 5/2000 | Geng | 348/36 |
| 6,130,958 | A | 10/2000 | Rohler | |
| 7,277,187 | B2 * | 10/2007 | Smith et al. | 356/601 |
| 2008/0152192 | A1 * | 6/2008 | Zhu et al. | 382/103 |
| 2009/0273792 | A1 | 11/2009 | Hullin et al. | |
| 2010/0110068 | A1 * | 5/2010 | Yamauchi et al. | 345/419 |
| 2010/0113921 | A1 | 5/2010 | Fear et al. | |
| 2011/0004207 | A1 * | 1/2011 | Wallace | A61B 5/4893 606/35 |
| 2011/0109725 | A1 * | 5/2011 | Yu et al. | 348/47 |
| 2012/0092461 | A1 * | 4/2012 | Fisker et al. | 348/46 |

OTHER PUBLICATIONS

Brown, "S Survey of Image Registration Techniques," ACM Computing Surveys, vol. 24, No. 4, Dec. 1992, 325-376.

Glasbey, et al, "A Review of Image-Warping Methods," Journal of Applied Statistics, vol. 25, No. 2, 1998,155-171.

Goshtasby, "Piecewise Linear Mapping Functions for Image Registration," Pattern Recognition, vol. 19, No. 6, 459-466.

Goshtasby, "Image Registration by Local Approximation Methods," Image and Vision Computing, vol. 6, No. 4, Nov. 1988, 255-261.

Yamashita, "3-D Measurement of Objects in a Cylindrical Glass Water Tank with a Laser Range Finder," Proceeding of the 2003 IEE/RSJ, International Conference on Intelligent Robots and Systems, Las Vegas, Oct. 2003, 1578-1583.

Yamashita, "3-D Measurement of Objects in Unknown Aquatic Environments With a Laser Range Finder," Proceedings of the 2005 IEEE, International Conference on Robotics and Automation, Barcelona, Spain, Apr. 2005, 3912-3917.

Zagorchev, "A Comparative Study of Transformation Functions for Nonrigid Image Registration," IEEE Transactions on Image Processing, vol. 15, No. 3, Mar. 2006, 529-538.

* cited by examiner

3D SCANNING LASER SYSTEMS AND METHODS FOR DETERMINING SURFACE GEOMETRY OF AN IMMERSED OBJECT IN A TRANSPARENT CYLINDRICAL GLASS TANK

RELATED APPLICATIONS

The application is a continuation of PCT Patent Application PCT/US2011/041448, filed Jun. 22, 2011 which claims priority to U.S. Provisional Patent Application 61/357,785, filed 23 Jun. 2010, the disclosures of which are incorporated herein by reference.

U.S. GOVERNMENT RIGHTS

The U.S. Government has certain rights in this invention as provided for by the terms provided by the National Institute of Health/National Cancer Institute for grant number PO1-CA080139.

BACKGROUND

Laser scanning of objects is typically performed through air. That is, the laser light passes through only one medium between a laser generator and the target object, and through the same medium between the object and an imaging camera. The object is typically rotated in the path of the laser line while the laser line generator and imaging camera remain stationary.

Objects, including human or mammalian breasts or limbs, must often be immersed in a fluid when ultrasound, microwave, or certain other imaging technologies are performed in order to optimize coupling of ultrasound and microwaves from transducers or antennae to the object. The fluid typically has a substantially different index of refraction than that of air, and light crossing boundaries of air to container, air to fluid, or container to fluid, is subject to refraction at those boundaries. Such refraction may cause substantial distortions in laser-scanned surface maps of the object. A. Yamashita, et al, *Proceedings of the* 2005 *IEEE International Conference on Robotics and Automation, Barcelona, Spain*, April 2005, 3-*D Measurement of Objects in Unknown Aquatic Environments with a Laser Range Finder*, illustrates that an object imaged in a cylindrical container of fluid is subject to substantial distortion. Yamashita then describes a procedure for triangulating points of a surface of the object as located by a laser rangefinder having a single laser and camera, then using ray tracing to correct such point locations to give corrected point locations.

While not historically used for image correction while measuring objects in fluid, image morphing has been used in other fields such as film. A. Gothalsby Piecewise Linear Mapping Functions For Image Registration, *Pattern Recognition*. Vol. 19, No. 6. pp. 459-466. 1986, describes methods for warping an image such that reference points in that image align to reference points in another image.

Where the object is an anatomical part of a human or other large mammalian subject, it can be undesirable to rotate the object.

SUMMARY OF THE INVENTION

In an embodiment, a system creates a 3D model of a surface of an object immersed in a transparent liquid within a stationary cylindrical transparent tank. The system includes a rotating mount aligned to rotate around a central axis of the cylindrical transparent tank, and a camera fixedly attached to the rotating mount for capturing images of the object immersed in the transparent fluid. The system also includes a first laser projector fixedly attached to the rotating mount for projecting a first laser line perpendicular to a rotational plane of the rotating mount and aligned to the central axis, the first laser projector being positioned at a first angle relative to a field of view of the camera, and a second laser projector fixedly attached to the rotating mount to project a second laser line perpendicular to the rotational plane and aligned to the central axis, the second laser projector being positioned at a second angle relative to the field of view. The system includes an actuator for rotating the rotating mount, a controller for driving the actuator to rotate the rotating mount and to capture images from the camera at selected angular positions of the rotating mount, and an image processor having either a ray tracing program or an image warping function implemented as machine executable instructions within the image processor, for processing the captured images. The image processor also has a coordinate extraction program for extracting a plurality of 3D positions where the laser lines are incident upon a surface of the object.

In another embodiment, a method generates a 3D model of a surface of an object immersed in a transparent liquid within a stationary cylindrical transparent tank. First and second laser line projectors and a camera are rotated around a central axis of the cylindrical tank. The first and second laser line projectors each generating a laser line perpendicular to a plane or rotation and aligned with the center of rotation. The camera images the object. An image from the camera is captured at each of a plurality of angular positions of the camera relative to a reference position of the stationary cylindrical tank. The captured images are processed to determine, for each laser line within each image, a plurality of 3D positions where the laser line is incident upon a surface of the object.

In another embodiment, a system images biological tissue with a microwave-frequency RF signal. The system includes a rotating 3D laser scanner and image processor for determining a surface geometry of the biological tissue within a cylindrical transparent tank. The system also includes a plurality of antennas retractable from the cylindrical transparent tank, one or more of the plurality of antennas configured for receiving the microwave-frequency RF signal, and a signal processor coupled to the receiving antennas and configured for processing a demodulated signal representative of the microwave-frequency RF signal received by the one or more of the plurality of antennas to model the dielectric properties of the biological tissue based upon the surface geometry.

In another embodiment, a method images biological tissue within a stationary cylindrical tank with a microwave-frequency RF signal. The biological tissue is scanned with a line laser and a camera to generate a plurality of images. The images are processed within an image processor to determine surface geometry of the biological tissue. The biological tissue is scanned using microwaves to generate a plurality of propagation measurements of the microwaves through the biological tissue, and dielectric properties of the biological tissue are modeled based upon the surface geometry and the propagation measurements.

DETAILED DESCRIPTION OF THE EMBODIMENTS

Figure 1:
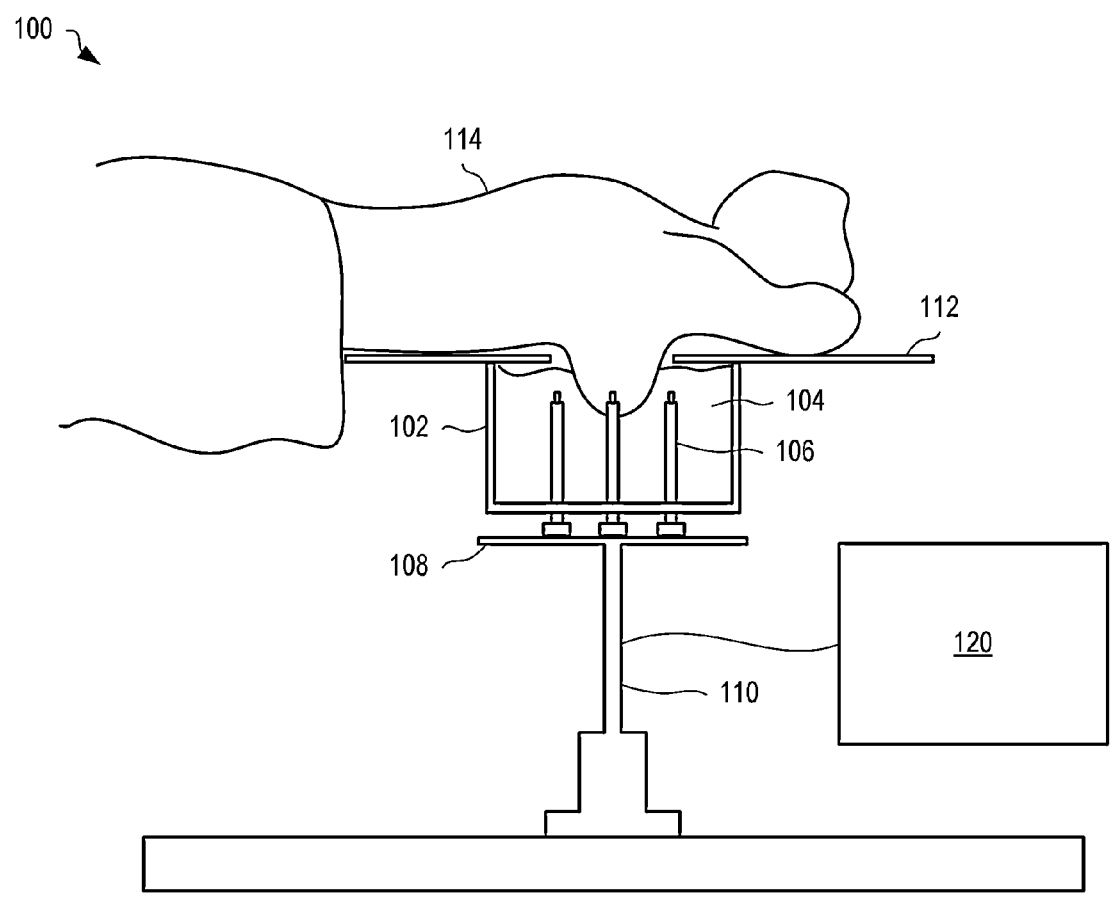
FIG. 1 is a schematic showing one exemplary prior art microwave imaging system for early detection of breast cancer that utilizes a transparent cylindrical tank containing a transparent fluid and an array of microwave antennae positioned within tank to pass low level microwaves through immersed breast tissue of a patient.

FIG. 1 is a schematic showing a prior exemplary microwave imaging system 100 for early detection of breast cancer that utilizes a transparent cylindrical tank 102 containing a transparent fluid 104 and an array of microwave antennae 106 positioned within tank 102 to pass low level microwaves through immersed breast tissue of a patient 114. Fluid 104 facilitates coupling of microwave-frequency RF signals from the antennas 102 to and through the breast tissue and back to antennas 102. System electronics 120 incorporates a microwave transmitter, a power divider, a switching network, microwave receivers, and a processor that cooperate to provide control over the operation of system 100 and the generation and reception of microwave signals through the array of antennas 106. Microwave imaging system 100 is described in detail within U.S. patent application Ser. No. 10/407,886, filed Apr. 4, 2003, and included within appendix A. Further details on the Microwave Imaging Spectroscopy Group can be found at URL: http://www-nml.dartmouth.edu/biomedprg/MIS/Main.html, and in a thesis by D. Li et al., titled "Microwave Imaging Spectroscopy for Breast Cancer Diagnosis" at Thayer School of Engineering, Hanover, N.H., May 2003.

The array of antennas transmits and receives microwave-frequency RF signals that are propagated through the biological tissue. A signal processor is coupled to the antennae to process a demodulated signal representative of the microwave-frequency RF signal received by one or more of the antennas to produce scattered field magnitude and phase signal projections of the biological tissue. These projections may be used to reconstruct a conductivity and permittivity image across an imaged section of the biological tissue to identify the locations of different tissue types (e.g., normal versus malignant or cancerous) within the biological tissue. The liquid coupling medium may include glycerol in a solution with water or saline, or in an emulsion with water, and oil and an emulsifier. The liquid coupling medium containing glycerol provides a low-contrast medium that is beneficial when imaging low-permittivity objects, such as human breast tissue.

The MIS group at Thayer is developing a new imaging modality for noninvasive early breast cancer detection. The group is part of the joint Breast Cancer Screening Project between the Thayer School of Engineering and the Dartmouth-Hitchcock Medical Center.

MIS makes use of low level microwave signals to study the composition and distribution of inclusions in dielectric materials, such as breast tissue. Signals are recorded indicative of scattering as the microwaves propagate through the tissue; then, using an iterative model based program, images are constructed that depict the dielectric properties, and inclusions and nonuniformities of those properties, necessary to produce the observed scattering.

The MIS system is self-contained within a specialized clinical bed—the breast is held pendent through an aperture in the bed and immersed in an aqueous glycerin bath. A circular array of 16 antennas is positioned around the breast, with each antenna sequentially acting as a transmitter while the others receive. Image reconstruction requires the spatial definition of two zones within the imaging plane—the target region (breast) and surrounding homogeneous region (bath). Resolution within the target region increases dramatically as the boundary of the two zones approaches the actual breast surface boundary (see FIG. 2).

The glycerin bath is intended to match the dielectric properties of the tissue as closely as possible. This reduces reflections of the microwaves off of the breast's surface and allows for the desired scattering effect. At the same time, the breast/bath boundary is effectively hidden from the scanner and must be estimated to enable accurate reconstruction of images of inclusions within the breasts, and to allow for accurate depiction of those inclusions relative to the breast surface.

Figure 2:
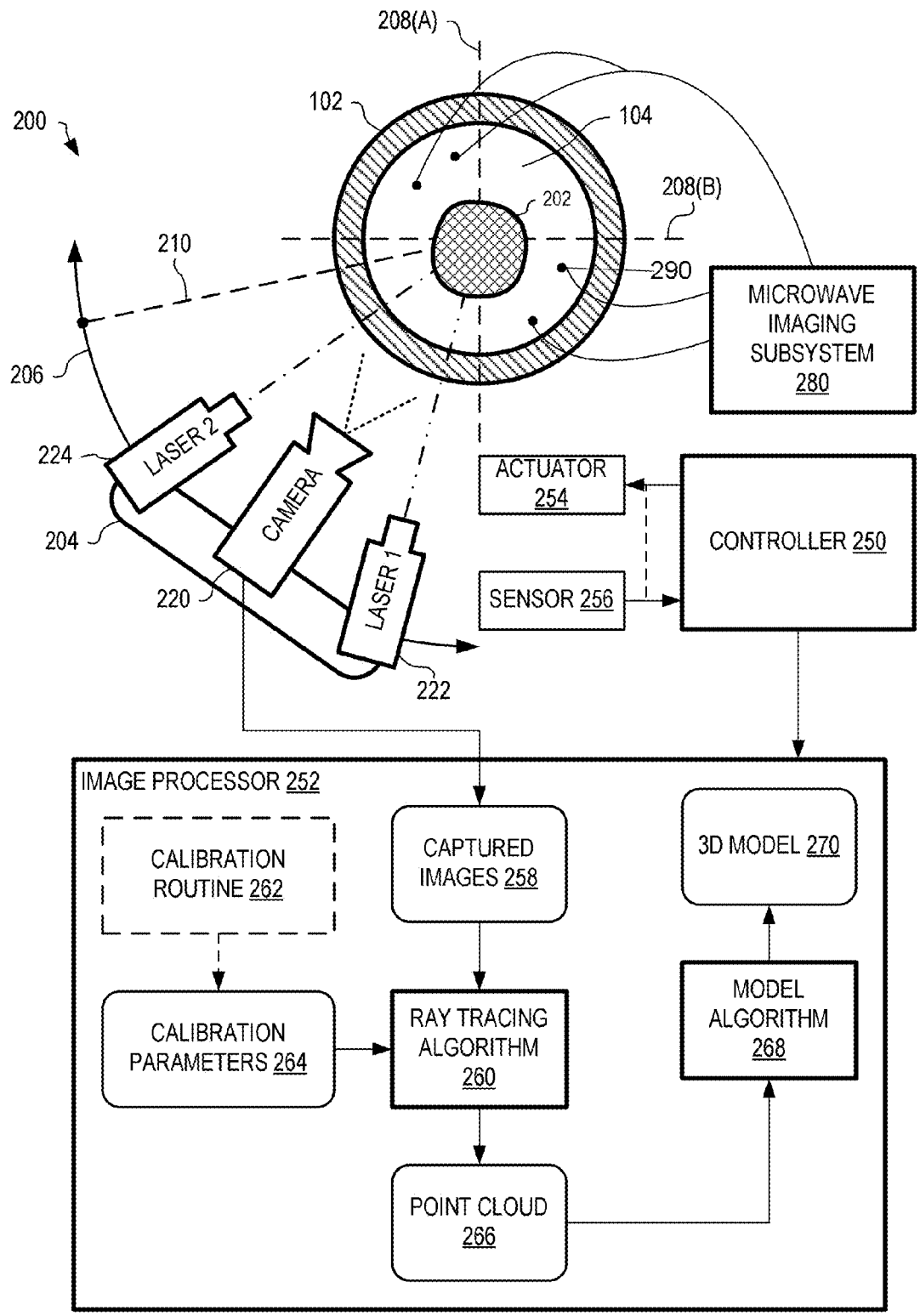
FIG. 2 shows an exemplary 3D scanning laser system for determining surface geometry of an object immersed in a transparent cylindrical glass tank.

FIG. 2 shows an exemplary 3D scanning laser system 200 for determining surface geometry of an immersed object in a transparent cylindrical glass tank. We propose combining the scanning laser system 200 of FIG. 2 with the microwave imaging device 100 of FIG. 1 to produce an improved microwave imaging device having enhanced accuracy, sensitivity, and specificity. System 200 includes a controller 250, an image processor, 252, a camera 220 and two laser line generators 222 and 224. Laser line generators, as used herein, may be implemented as a point laser with 2-D deflection or as a point laser with a holographic linear spreader. Camera 220 is mounted on a rotating mount 204 that rotates around a central axis aligned with a central axis of a stationary transparent cylindrical tank 102. This central axis is indicated by cross-hairs 208(A) and 208(B). In an embodiment, laser line generators 222 and 224 generate laser lines of different colors to make them easy to differentiate in the captured (color) images. That is, wavelength of each laser line may be differentiated with a color camera. In an example, while imaging objects that are off-center of the imaging tank, it is possible for the laser lines to intersect and/or cross before they project onto the object's surface. Without prior knowledge of the shape and position of the object, it would be difficult to differentiate between the two laser lines if they were of the same color (or if they were captured in black and white). In an alternate embodiment, laser line generators 222 and 224 are activated to alternately generate a laser line, and camera 220 captures images of each laser line separately, thereby alleviating problems of discerning which laser line is due to which laser line generator, as may occur when both laser line generators are fired simultaneously or continuously.

Figure 3:
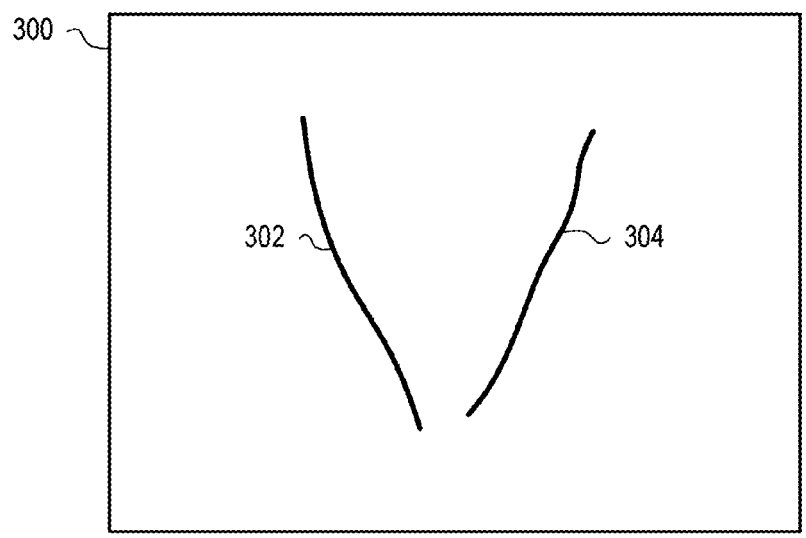
FIG. 3 shows one exemplary image of laser lines incident upon an object at one specific position of the rotating mount of system 200, FIG. 2.

An actuator 254, under control of controller 250, rotates rotating mount 204 around tank 102, and camera 220 and image processor 252 cooperates, under control of controller 250, to capture a plurality of images 258 from camera 220. Specifically, controller 250 utilizes a rotating mount position reported by sensor 256 to capture images 258 at selected positions (e.g., at 360 equally spaced positions) of rotating mount 204 around tank 102. FIG. 3 shows one exemplary image 300 captured by camera 220 of laser line images 302 and 304 resultant from incidence of laser lines generated by laser line generators 224 and 222, respectively, upon object 202 at one specific position of rotating mount 204, where the object may be a human breast.

In an embodiment, since the motion of rotating mount 204 is constrained to only one degree of freedom (rotation in a horizontal plane about tank 102), the types of objects that can be successfully modeled by system 200 is limited. For example, features of objects with large convexities and/or concavities may hide at least part of a laser line from the camera's point of view (POV). By including a second laser line generator that operates at a second angle from camera 220, a second POV is added and the camera's entire field of view is utilized. Features that are hidden from one POV can often be seen from the other, increasing the number of shapes that may be successfully imaged.

Figure 4:
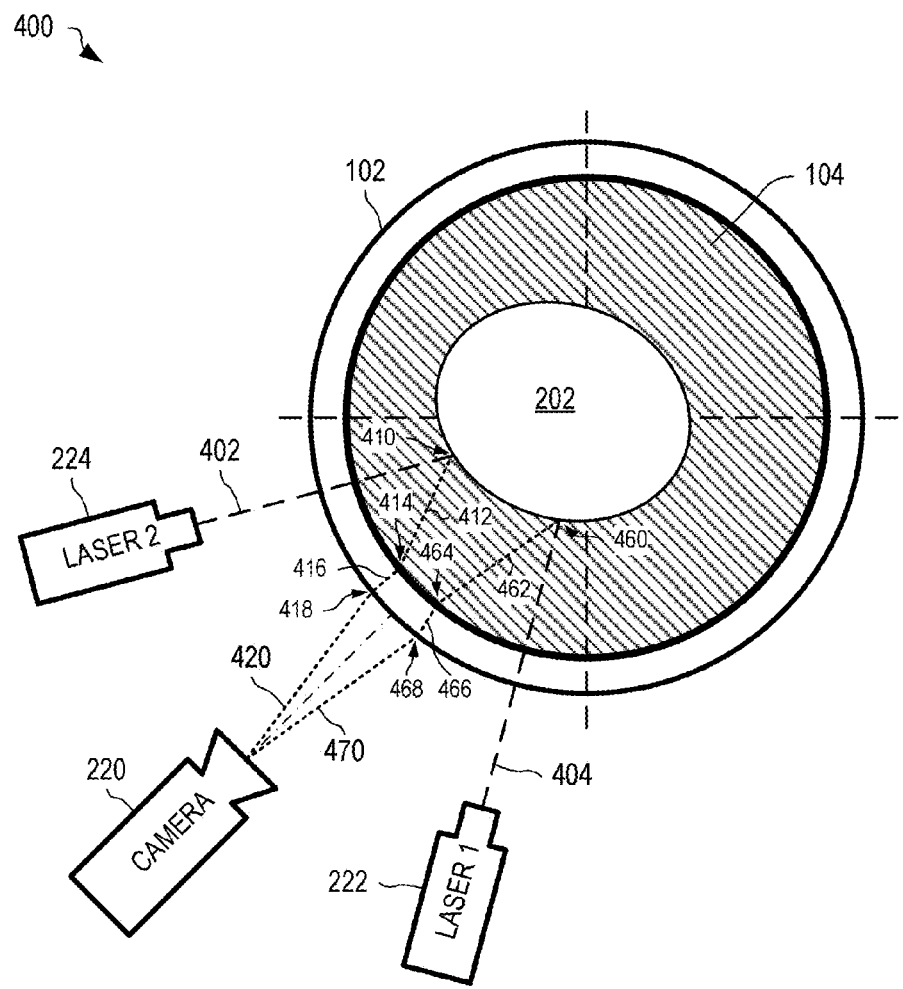
FIG. 4 is a schematic diagram illustrating exemplary paths of laser lines, generated by the laser line generators of FIG. 2, as they pass through air, the transparent tank, and the transparent fluid to become incident upon a surface of the object.

FIG. 4 is a schematic diagram illustrating exemplary paths of laser lines 402 and 404, generated by laser line generators 224 and 222, as they pass through air, transparent tank 102, transparent fluid 104 to become incident upon a surface of object 202 at points 410 and 460, respectively. Since laser lines 402 and 404 are aligned to the central axis of tank 102, no angular change results from diffraction through tank 102 and transparent fluid 104. In an embodiment, image processor 525 operates under control of a ray tracing routine or program 260 to determine paths for rays of detected laser line images 302 and 304 within each image 300 of images 258 to determine incident points 410 and 460, and hence a surface position of object 202.

Specifically, ray tracing program 260 utilizes Snell's Law, the refractive index of the transparent cylindrical tank, known dimensions (e.g., internal diameter and external diameter) of tank 102, intrinsic camera properties, such as focal length, the refractive index of the transparent fluid 104, calibration parameters 264, and captured images 258 to determine a point cloud 266 defining the surface of object 202. Calibration parameters 264 include characteristics of camera 220 and movement of rotating mount 204 around tank 102. Given the position (e.g., pixel locations) of laser line images 302 and 304 within image 300, program 260 determines a plurality of rays (e.g., rays depicted by segments 412, 416, 420, and 462, 466, 470 within FIG. 4) and a location (e.g., points 410 and 460) where each ray is incident upon object 202. Program 260 relies upon precise knowledge of both the intrinsic and extrinsic camera properties (as stored in calibration parameters 264), which are determined using a calibration process (described below) during the scanner's assembly.

Figure 2A:
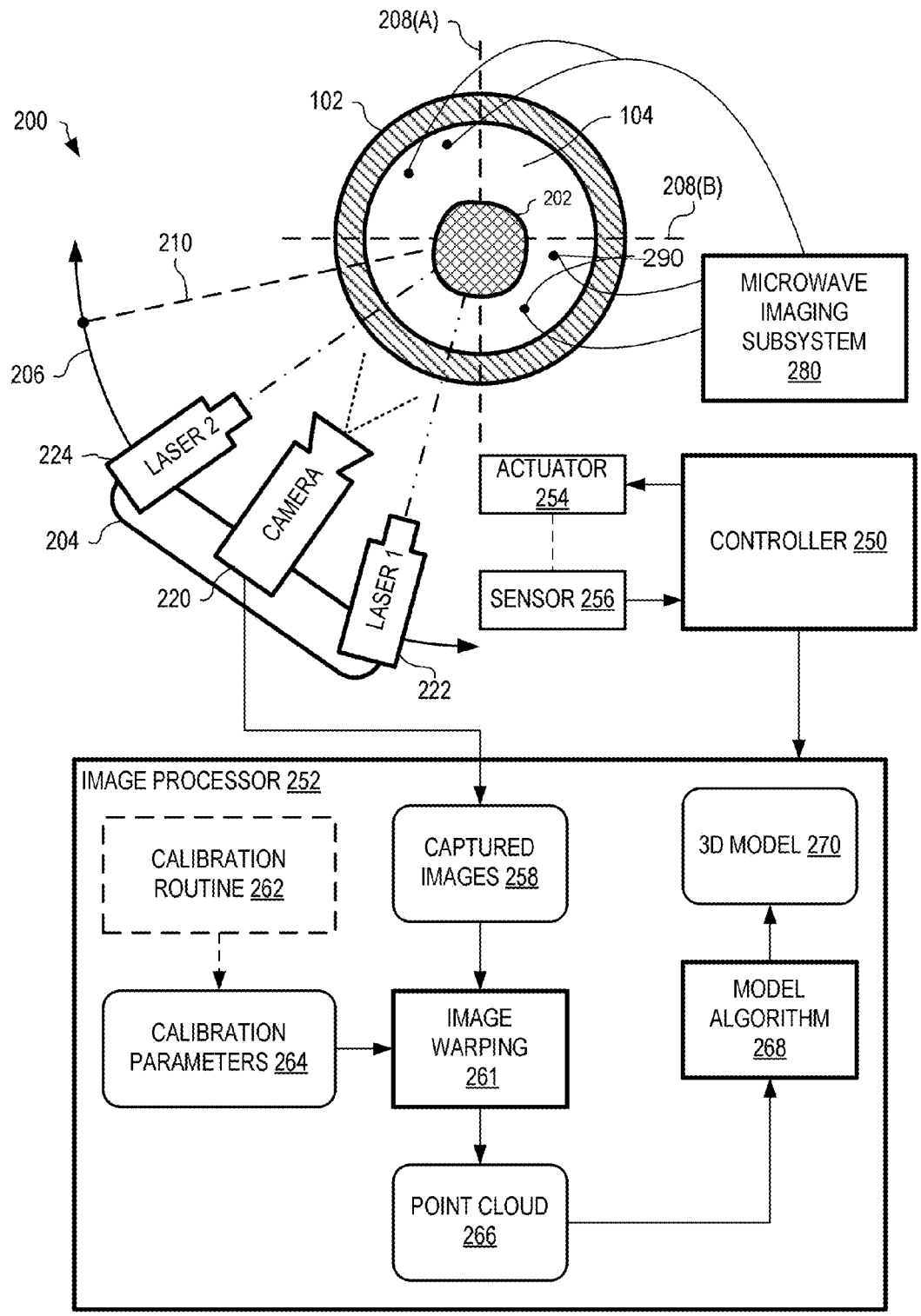
FIG. 2A shows an exemplary 3D scanning laser system for determining surface geometry and performing microwave imaging of an object immersed in a transparent cylindrical glass tank, the surface geometry corrected for refraction by image warping.

In an alternative embodiment, as illustrated in FIG. 2A, image processor 258 uses machine readable instructions for performing image warping 261 on images obtained by camera 220 to provide corrected or "registered" images instead of using ray tracing program 260; the warping 261 serves to correct for distortions introduced by refraction. In this alternative embodiment, an image warping function F for correcting an image is determined during a calibration phase, then function F is applied to captured images 258 prior to determining point cloud 266. In this alternative embodiment, no ray tracing need be done because the warping function F suffices to correct for refractive errors; other hardware of the imaging system, and steps performed by the image processor 258, remain the same as previously described with reference to FIG. 2. In a particular embodiment, the image warping function F is determined during calibration during assembly of the system, in an alternative embodiment capable of compensating for variations in fluid concentration and composition, the image warping function F is determined during a calibration phase after adding fluid to the container and before imaging the object.

Some prior image warping functions are described in C Glasbey, et al., A review of Image-Warping Methods, *Journal of Applied Statistics*, Vol. 25, No. 2, 1998, 155-171.

In various embodiments, Image warping function F may include one of Polynomial Registration, Piecewise Linear Regression, Local Weighted Mean Registration, or Thin Plate Mean Regression. In a particular embodiment, Local Weighted Mean Regression was implemented using second-order polynomials in image warping function F with some success.

Figure 6:
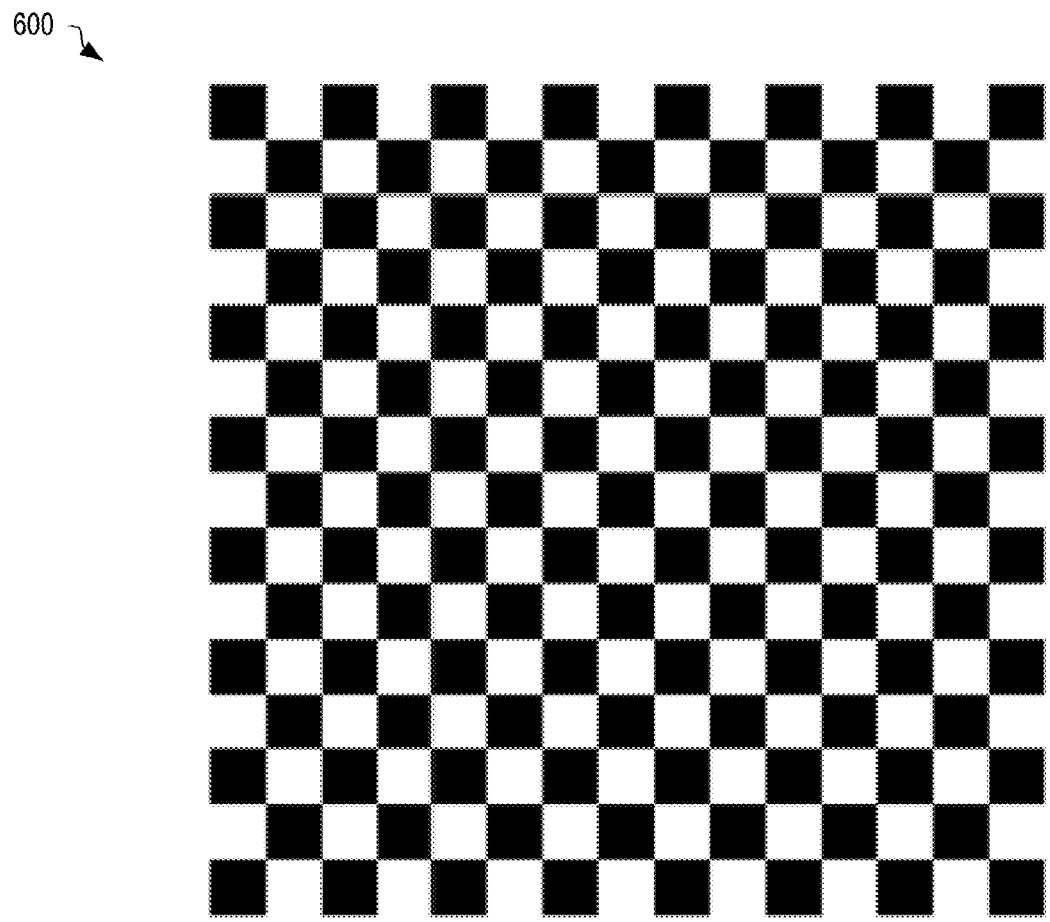
FIG. 6 shows one exemplary test grid, formed as a 15 by 15 array of alternating black and white squares, for calibrating the system of FIG. 2.

Calibration of image warping function F was performed by placing a reference object, which in an embodiment is a card printed with a checkerboard as illustrated in FIG. 6 in the fluid 104 in tank 102, extracting vertexes at corners of shapes of the checkerboard from images produced by camera 220, and fitting parameters of the image warping function F to produce a function that mapped these images into real space.

Polynomial Registration:

Global polynomial registration attempts to find a single polynomial function that can correctly map one image space onto another. This technique utilizes control point pairs and can take on many forms. In an alternative embodiment, second and third order bivariate polynomials of the form $a \cdot x^n \cdot y^m$, are fit to the control point pairs using a least-squares approximation. The $n^{th}$ order polynomial is given by the equation:

$$T(x, y) = \sum_{j=0}^{n} \sum_{k=0}^{j} A_{jk} x^k y^{j-k} \qquad \text{Equation 1}$$

Given N control point pairs $((x_i, y_i)$ in the image and $(X_i, Y_i)$ in the grid), the coefficients $A_{jk}$ can be found for a least squares fit by solving the system of linear equations:

$$\begin{bmatrix} A_{00} \\ A_{10} \\ A_{11} \\ \vdots \\ A_{nn} \end{bmatrix} \begin{bmatrix} 1 & x_1^1 y_1^0 & x_1^0 y_1^1 & \cdots & x_1^n y_1^n \\ 1 & x_2^1 y_2^0 & x_2^0 y_2^1 & \cdots & x_2^n y_2^n \\ \vdots & \vdots & \vdots & & \vdots \\ 1 & x_N^1 y_N^0 & x_N^0 y_N^1 & \cdots & x_N^n y_N^n \end{bmatrix}^{-1} \begin{bmatrix} X_1 \\ X_2 \\ \vdots \\ X_N \end{bmatrix}$$

Equation 2

This system of equations can be solved as long as N is not less than the polynomial order n. For N greater than n, the pseudo-inverse of the center matrix is used and a least squares approximation found. While second and third order polynomials can be appropriate for global deformations of low spatial frequency, they are prone to miss-approximating local deformations. Higher order polynomials may be used but are prone to high fluctuations in the interpolated values that rarely fit the required registration transformation.

Piecewise Linear Regression:

Piecewise linear image registration methods were described by Goshtasby. In this technique, control points in the fixed image are triangulated (most commonly using a Delaunay triangulation method) and matched to corresponding points and triangles in the moving image. A linear transformation is then used to map each triangle from one image to the other. Such transformations have the advantage of detecting local deformations that global transformations would miss—as long as the regions are small with respect to the geometric scale of the deformations. Like all interpolation methods, control point mapping is exact. Mapping of the regions forms a continuous but not necessarily smooth function; in addition, regions outside the span of the triangulation (the convex hull) must rely on extrapolation to complete the transformation. Extrapolation to areas far from control points may lead to large errors in the registration.

Local Weighted Mean Registration:

The local weighted mean (LWM) method attempts to combine the benefits of the previous two methods—uniting the smooth function nature of polynomials and the local sensitivity of piecewise functions. This method attempts to fit a $N^{th}$ order polynomial to each control point such that the function fits each point and its N−1 nearest control point neighbors. The value at any point (x,y) is then the weighted mean of the polynomials passing over that point, such that the image transformation T(x,y) is given by:

$$T(x, y) = \frac{\sum_i W_i \cdot P_i(x, y)}{\sum_i W_i}$$

Equation 3

Where $P_i(x,y)$ is the polynomial corresponding to the $i^{th}$ control point and $W_i$ is simply a weight relating to the distance between the point of interest (x,y) and the $i^{th}$ control point—larger weights are assigned to nearer control points. In this way, the polynomials corresponding to closer control points will have the greatest influence. The resulting transformation is smooth at all points and considerably more sensitive to local deformations than the global least squares polynomial transformation.

Thin-Plate-Spline Registration:

This registration method models the transformation as a deformation of a thin plate of infinite extent. Loads of varying intensity and direction are applied and centered at each of the control points. A stiffness or smoothing parameter is often utilized to control the amount of deformation caused by the loads. The TPS is another example of a global transformation and it is limited in its ability to accurately model large local deformations.

The smoothing (or approximating) thin plate spline defined in the following equation was used to compare this registration technique with the other methods:

$$T(x, y) = A_0 + A_1 x + A_2 y + \sum_i B_i r_i^2 \ln r_i^2$$

Equation 4

Where $r_i^2$ is the Euclidean distance to the $i^{th}$ control point and the coefficients $A_i$ and $B_i$ are chosen to minimize the sum:

$$p \sum_i E_i(T) +$$
$$(1-p) \int \int_{-\infty}^{\infty} \left\{ \left(\frac{\partial^2 T}{\partial x^2}\right)^2 + \left(\frac{\partial^2 T}{\partial x \partial y}\right)^2 + \left(\frac{\partial^2 T}{\partial y^2}\right)^2 \right\} dx dy$$

Equation 5

Here, $E_i$ is the Euclidean norm of $T(x_i,y_i)$ to its corresponding control point $(X_i,Y_i)$ and p denotes a smoothing parameter that varies from 0 to 1 and determines the stiffness of the spline. Values of p close to 1 result in an interpolating spline (least squares fit) whereas values close to 0 result in complete smoothing and approximations at the control points.

Each of these methods can effectively be used to create an algorithm for finding the surface of an object in the imaging tank. We performed an analysis of all methods to see which would produce the most accurate results. Each of the image registration techniques described above outperformed the ray tracing algorithm previously employed. Ultimately, we chose to utilize the local weighted mean method as it provided the greatest accuracy (an average error of approximately 0.14 mm at each calculated point).

In the embodiment of FIG. 2A, once calibrated image warping is complete, image processor 258 performs a three-dimensional coordinate triangulation and extraction function to generate a point cloud.

With reference to FIG. 2 and FIG. 2A, once a point cloud is generated by calibrated ray tracing or calibrated image warping and coordinate triangulation, image processor 258 performs a model-generation program 268 to process point cloud 266 to generate a 3D model 270 of object 202 that defines the surface geometry of object 202 immersed within transparent fluid 104 in transparent cylindrical tank 102. In an embodiment, 3D model 270 is a finite element mesh.

Other subsystems of microwave imaging system 100, FIG. 1 use 3D model 270 when processing images of object 202 immersed within tank 102. For example, microwave imaging system 280 provides microwave energy to each antenna of an array of antennae 290 in sequence, while measuring responses at each other antenna of antennae 290. A microwave model of dielectric properties of the fluid and breast is constructed that is constrained to have uniform dielectric properties external to the space defined by 3D model of the breast, and permitted to have variable dielectric properties representing nonuniformities and inclusions within the space defined by the 3D model of the breast. A three-dimensional model of these properties is then constructed by fitting the dielectric properties of the model to the measured date. The system 100 of FIG. 1 may therefore provide microwave analysis of improved quality and reliability when using measurements determined from 3D model 270 in addition to microwave measurements made when imaging patient 114. 3D model 270 allows system 100 to model low level microwave signal propagation through breast tissue more accurately since the location of the boundary between the breast and the transparent fluid 104 is accurately known, and signal diffraction at that boundary may be accurately modeled. Further, reconstruction may be improved by excluding solutions that incorporate inclusions external to the breast.

Object 102 (i.e., patient 114), transparent fluid 104, and tank 102 are static for reasons of practicality, thus rotating mount 204, laser line generators 222 and 224, and camera 220 are mounted to revolve around tank 102 (i.e., the central axis) in a fixed plane. The use of two different color laser lines incident upon object 102 within the field of view of camera 220 allow additional detail to be determined from each image captures at selected angles of rotating mount 204 around tank 102.

In an embodiment, controller 250 is implemented using a custom LabVIEW program operating on a computer that controls operation of system 200 by driving actuator 254 (implemented as a stepper motor) and acquiring images 258 from camera 220. Sensor 256 is implemented as an optical encoder on actuator 254 (e.g., on the stepper motor) that is read by controller 250 to ensure that the position of rotating mount 204 (and by association camera 220 and laser line generators 222 and 224) is always known. Controller 250 may execute pre-programmed scans at various resolutions, as well as allow independent manual operation of all stepper motor and camera functions. A typical scan lasts approximately 30 seconds and acquires images using camera 220 in one degree intervals over a full 360 degree rotation of rotating mount 204.

In an embodiment, ray tracing program 260 is implemented as a Matlab toolbox running on a computer to read in captured images 258 from camera 220, extract points off the laser line images 302 and 304 therein, and performs ray tracing to determine three dimensional points where laser lines are incident upon the surface of object 202. By combining points derived from all captured images 258, point cloud 266 is generated to represent object 202 (e.g., the breast surface as it is oriented within the MIS system 100).

In an embodiment, model program 268 is implemented using SolidWorks (or other CAD/meshing software) operating on the computer to process point cloud 266 and generate 3D model 270 as a finite element mesh of the surface of object 202 (i.e., the breast of patient 114 being scanned by system 100).

Additional information can be found in a appendix B, which is a paper titled "3-D Measurement of Objects in a Cylindrical Glass Water Tank with a Laser Range Finder", by Yamashita, et al., Proceedings of the 2003 IEEE/RSJ, October 2003.

After a subject has been placed such that her breast is suspended in the fluid, and a three-dimensional model 270 has been constructed of her breast surface, an additional imaging system such as microwave imaging system then records images of the breast and uses the three-dimensional model 270 during image reconstruction.

Figure 5:
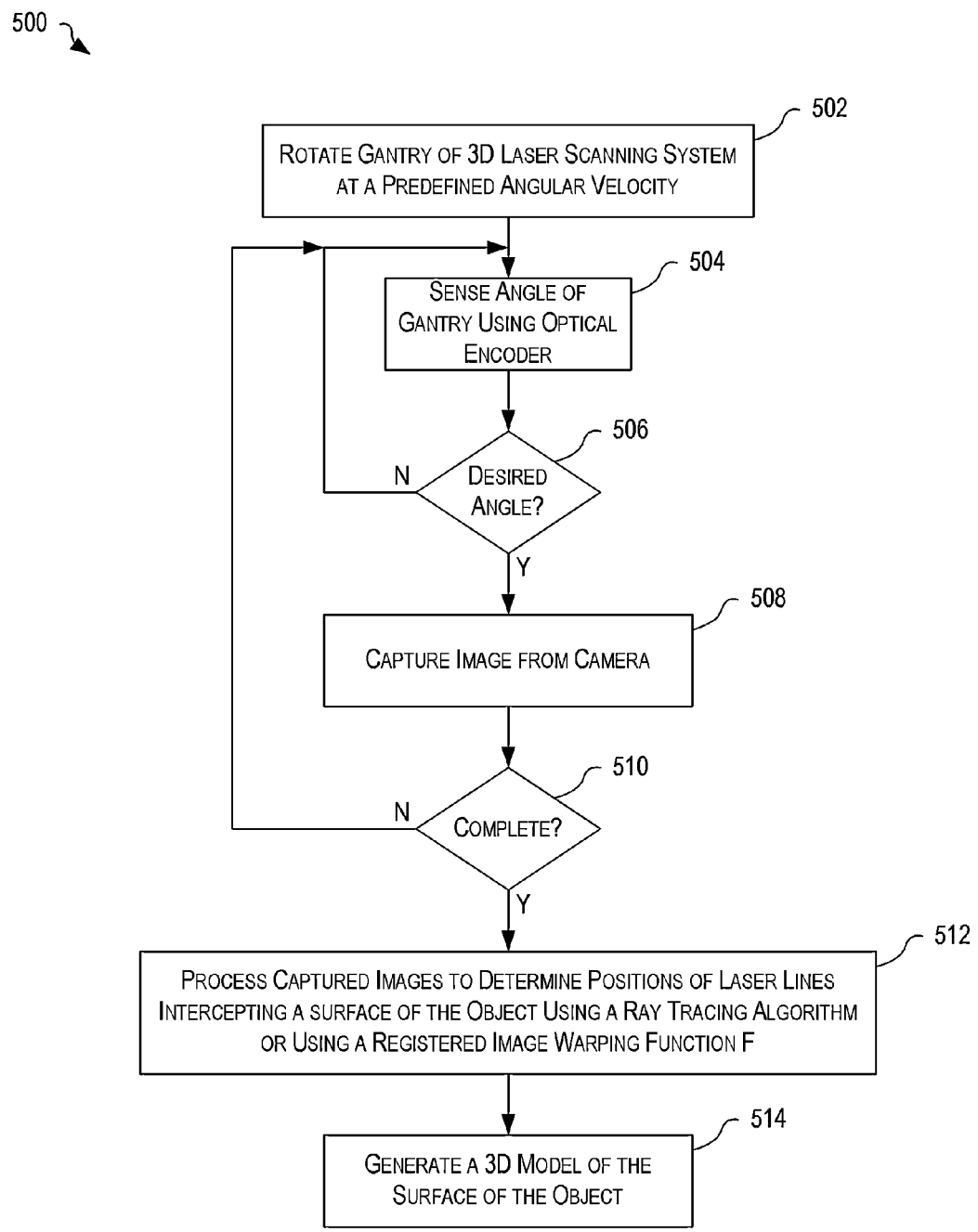
FIG. 5 is a flowchart illustrating one exemplary process for determining surface geometry of an immersed object in a transparent cylindrical tank, in an embodiment.

FIG. 5 is a flowchart illustrating one exemplary process 500 for determining surface geometry of an immersed object in a transparent cylindrical tank. In step 502, process 500 rotates a rotating mount of a 3D laser scanning system at a predefined angular velocity. In one example of step 502, controller 250 operates actuator 254 to rotate rotating mount 204 around the central axis of tank 102 at an angular velocity of 12 degrees per second.

As the rotating mount, or gantry, is rotated, its angular position is sensed 504 using an optical encoder. At several predetermined angles of the gantry, images are captured 508. Each captured image is stored for processing. Once images are captured 508 at all predetermined angles, image capture is complete 510. Then, the captured images are processed to correct them using either the ray tracing algorithm 260 or the registered image warping function F 261. Point locations are then extracted by triangulation from the images, and a three-dimensional surface model of the breast is generated 514.

Calibration Process

System 200 includes a calibration routine 262 that is initiated by controller 250 to calibrate system 200 prior to use. Specifically, calibration may occur only once during assembly of system 200, and can be considered a two step process; alternatively calibration may be repeated after filling of the tank with fluid. FIG. 6 shows one exemplary test grid 600 formed as a 15 by 15 array of alternating black and white squares. In an embodiment, each square has sides of one centimeter. The calibration routine is based upon a MATLAB Camera Calibration Toolbox developed by Jean-Yves Bouguet at the California Institute of Technology. See http://www.vision.caltech.edu/bouguetj/calib_doc/htmls/example.html.

In ray-tracing embodiments, calibration routine 262 models camera 220, which has a fixed focal length, as a "pinhole camera" whereby all light rays pass through the focal point of the camera and project onto the image plane of the camera sensor. This model accounts for lens distortions and the extrinsic positioning of the camera in space.

In a first step, calibration routine 262 determines "intrinsic camera parameters" such as a focal length, CCD skew, and CCD offset by capturing a series of images (all within focus and including the entire surface of the test grid) of test grid 600 when positioned over a range of distances and angles relative to camera 220. This first calibration step may be performed prior to mounting camera 220 to rotating mount 204. Calibration routine 262 extracts the locations of the grid corners from each captured image and determines the intrinsic parameters, stored within calibration parameters 264, for use by ray tracing program 260.

In image-warping embodiments, calibration of image warping function F is performed by placing a checkerboard as illustrated in FIG. 6 at a known location and angle in the fluid 104 in tank 102, extracting vertexes at corners of shapes of the checkerboard from images produced by camera 220, and fitting parameters of the image warping function F to produce a function that mapped these images into real space producing a corrected image of the checkerboard at correct location and angle.

In a second step, calibration routine 262 determines "extrinsic camera parameters" based upon rotation and translation of camera 220 as it rotates around tank 102 on rotating mount 204. In an embodiment, these parameters are based upon an origin of system 200 formed as the top center of tank 102. With camera 220 mounted to rotating mount 204, and without tank 102 in place, reference object or calibration grid 600 is aligned with the central axis and made coplanar with the laser line projection plane of laser line generator 222 and a single image of grid 600 is captured using camera 220. The grid 600 is then aligned with the central axis and made coplanar with the laser line projection plane of laser line generator 224 and another image of grid 600 is captured using camera 220. The Calibration Toolbox then analyses the images and determines extrinsic parameters, from which the angles and distances between the camera, the lasers, and the system origin can be determined. These parameters are also stored within calibration parameters 264 and used by ray tracing program 260.

In an embodiment, an additional step of calibration with tank 102 in place is performed to account for anomalies of the tank wall and within the transparent tank. Further calibration may be performed with tank 102 full of transparent fluid 104 to calibrate for variation in refractive index of transparent fluid 104. For example, such calibration may be beneficial when tank 102 has a diameter of less than twelve inches, when variation in tank wall thickness may affect accuracy of results.

Figure 7:
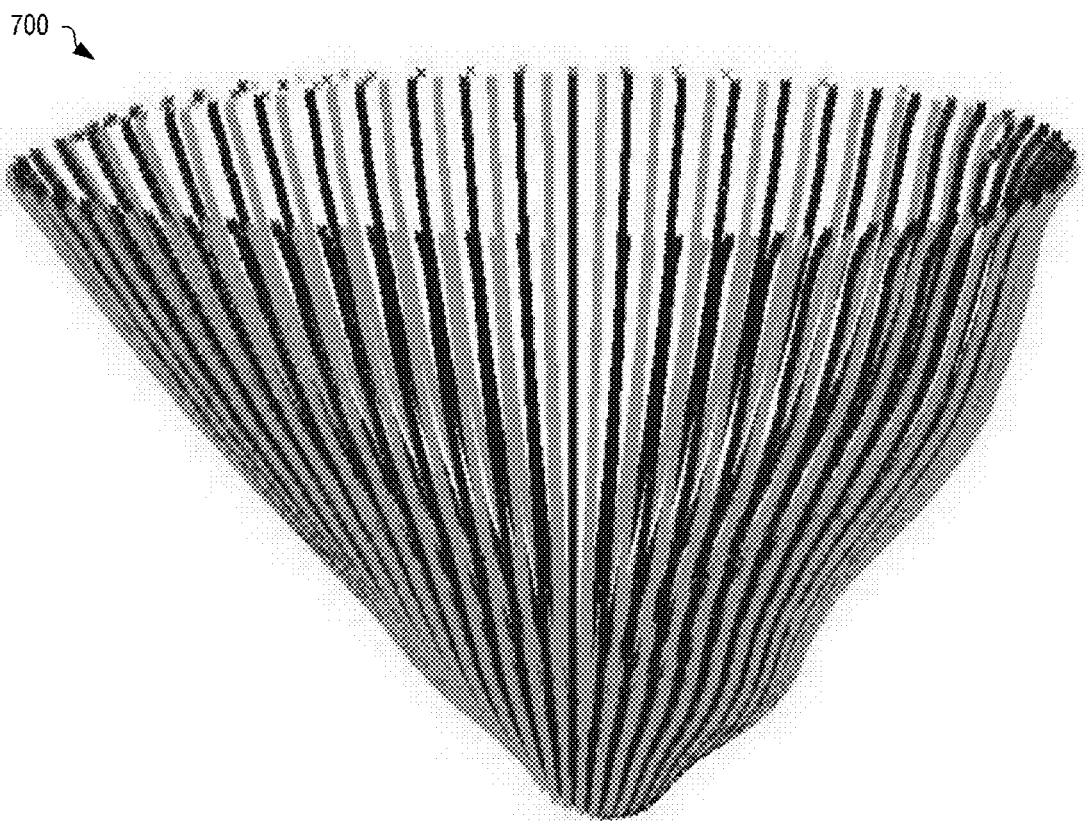
FIG. 7 shows one exemplary point cloud generated by the ray tracing program of the system of FIG. 2.
Figure 8:
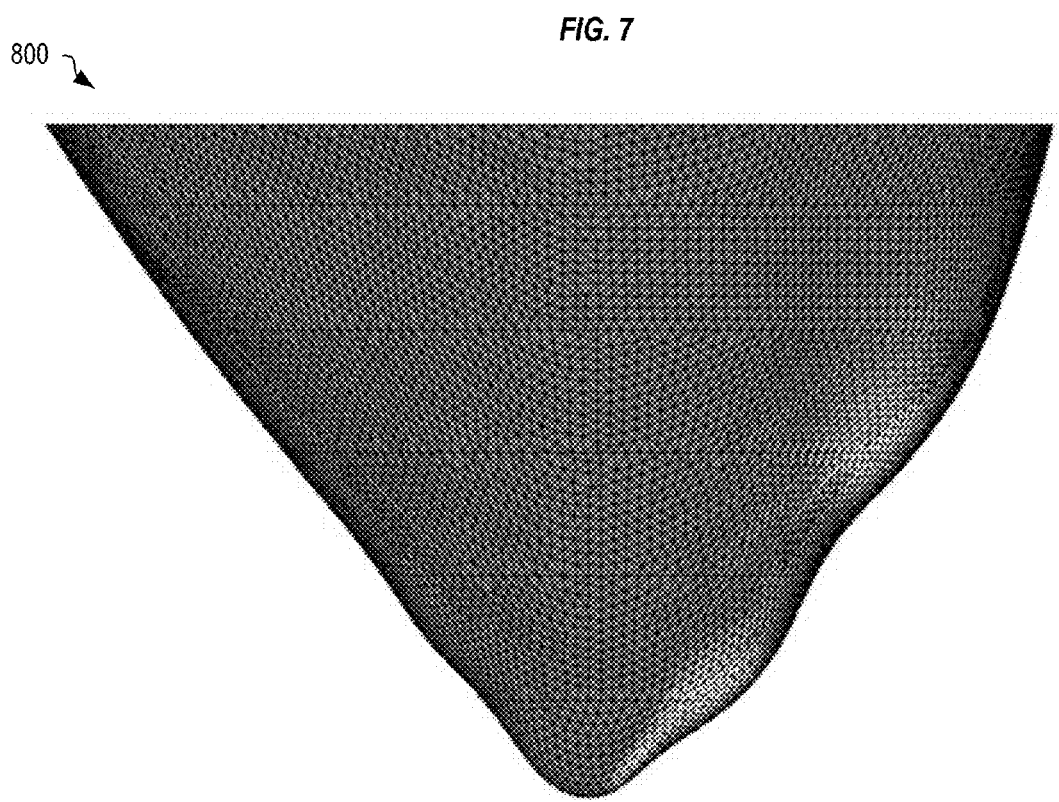
FIG. 8 shows one exemplary 3D model generated by the model program of the system of FIG. 2 from the point cloud of FIG. 7.

FIG. 7 shows one exemplary point cloud 700 generated by ray tracing program 260, FIG. 2, from captured images 258. Point cloud 700 may represent point cloud 266. Point cloud 700 clearly slows points plotted in 3D to illustrate the surface of object 202. FIG. 8 shows one exemplary 3D model 800 generated by model-generation program 268 from point cloud 700. 3D model 800 may represent 3D model 270.

Experimental Results

System 200 has been tested using plastic phantom target objects, calibration grids, and a glycerin bath, as used within MIS system 100. A plastic phantom target object is mounted through an aperture in the top of tank 102, in a manner similar to the positioning of patient 114 with system 100. System 200 has successfully captured the surface of the target to generate point cloud 266 with a coordinate system based upon the coordinate system of MIS system 100, and created a finite element surface mesh (i.e., 3D model 270) from the point cloud. Calibration grids (e.g., calibration grid 600) mounted within tank 102 and imaged by system 200 have been resolved to sub-millimeter accuracy at each calculated point, and with an average deviation of one millimeter across the entire field of view of camera 220. Utilizing system 200 to make a full 360 degree scan of an average sized object, such as a hemisphere of six inch diameter, and taking 360 images (i.e., images taken at one degree increments) generates point cloud 266 with approximately 300,000 points.

System 200 operates within the confines of MIS system 100 to image objects generally conical or semi-spherical in shape. As such, the motion of rotating mount 204 (i.e., camera 220, and laser line generators 222, 224) is limited to one plane of rotation. This prevents system 200 from accurately measuring the surface of objects with complex features. Traditional laser scanners rotate objects along two axes of rotation to detect features otherwise masked by large concavities or convexities in the surface of the object. Although limited to only one axis of rotation, system 200 accurately finds the surface of a breast within MIS system 100, but would have difficulty imaging a shape such as a human hand. System 200 may be enhanced to measure more complex shapes by either adding a second degree of motion to rotating mount 204, or by attaching an additional camera and one or more additional laser line generators to rotating mount 204 and configured at different angles of incidence from camera 220 and generators 222 and 224. However, for the intended use within MIS system 100 for measuring the surface of regularly shaped human breasts, system 200 has been shown to perform very well.

Ray tracing program 260 is optimized to work within the low light environment of MIS system 100, where it utilizes the high degree of contrast between the laser light and the ambient light to extracts points off the laser line images in captured images 258. However, ray tracing program 260 may be modified to operate in an environment with higher levels of ambient light if necessary.

Figure 9:
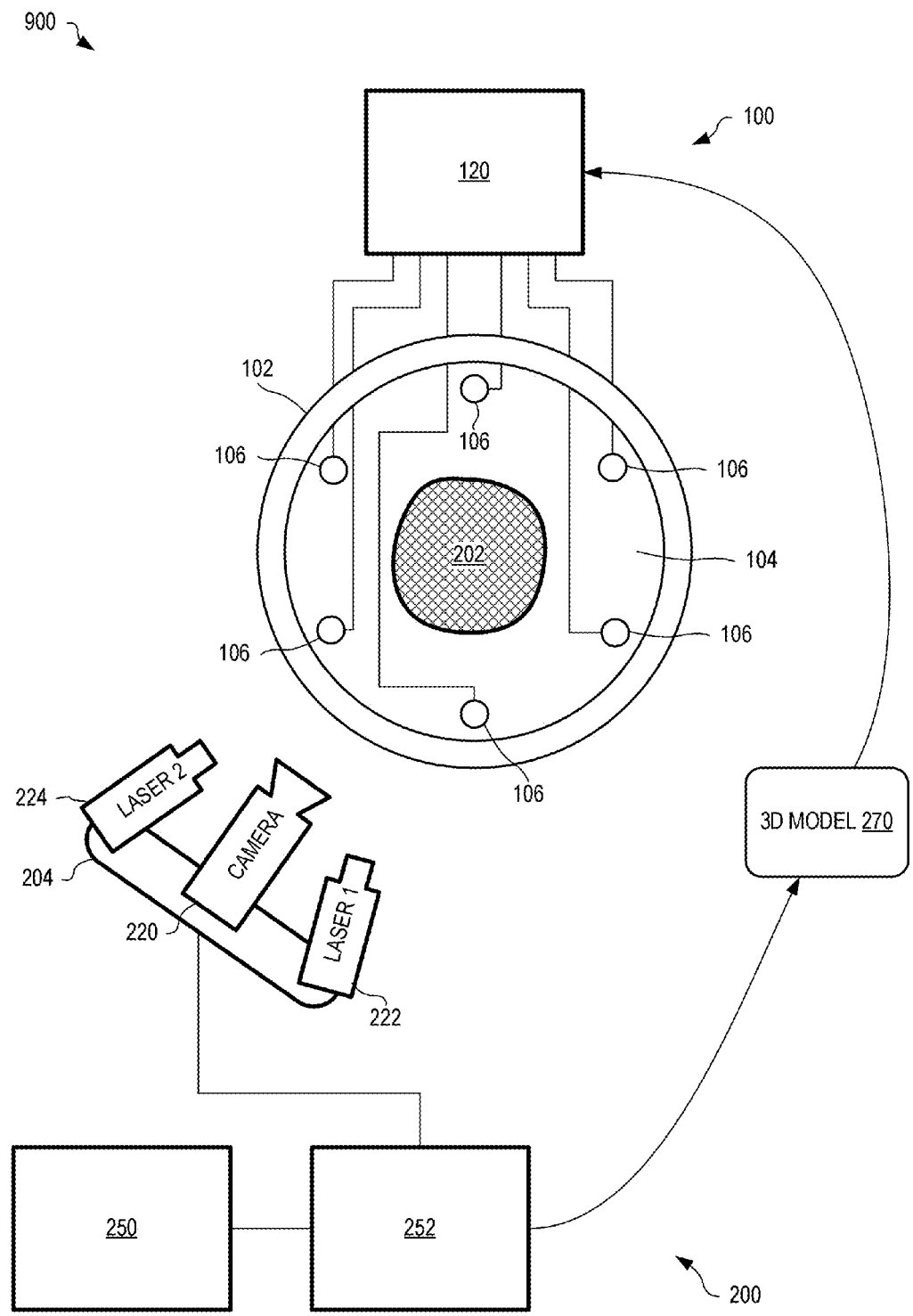
FIG. 9 shows the microwave imaging system of FIG. 1 and the 3D scanning laser system of FIG. 2 cooperating to improve microwave imaging of biological tissue using a microwave-frequency RF signal.

FIG. 9 shows system 100, FIG. 1 and system 200, FIG. 2, cooperating in a system 900 to improve microwave imaging of biological tissue using a microwave-frequency RF signal. Specifically, system 200 determines the surface geometry of object 202 immersed within transparent fluid 104 within tank 102 and generates a 3D model 270 defining the surface geometry of object 202. System electronics 120 of system 100 utilizes the defined surface geometry within 3D model 270 to improve modeling of microwave propagation through object 202. In particular, system 100 benefits from accurate definition of surface geometry of the object immersed within transparent fluid 104 of tank 102 to permit modeling of propagation of microwaves through object 202 more accurately and thereby provide earlier diagnosis of breast cancer, and improve specificity by reducing false positives.

Figure 10:
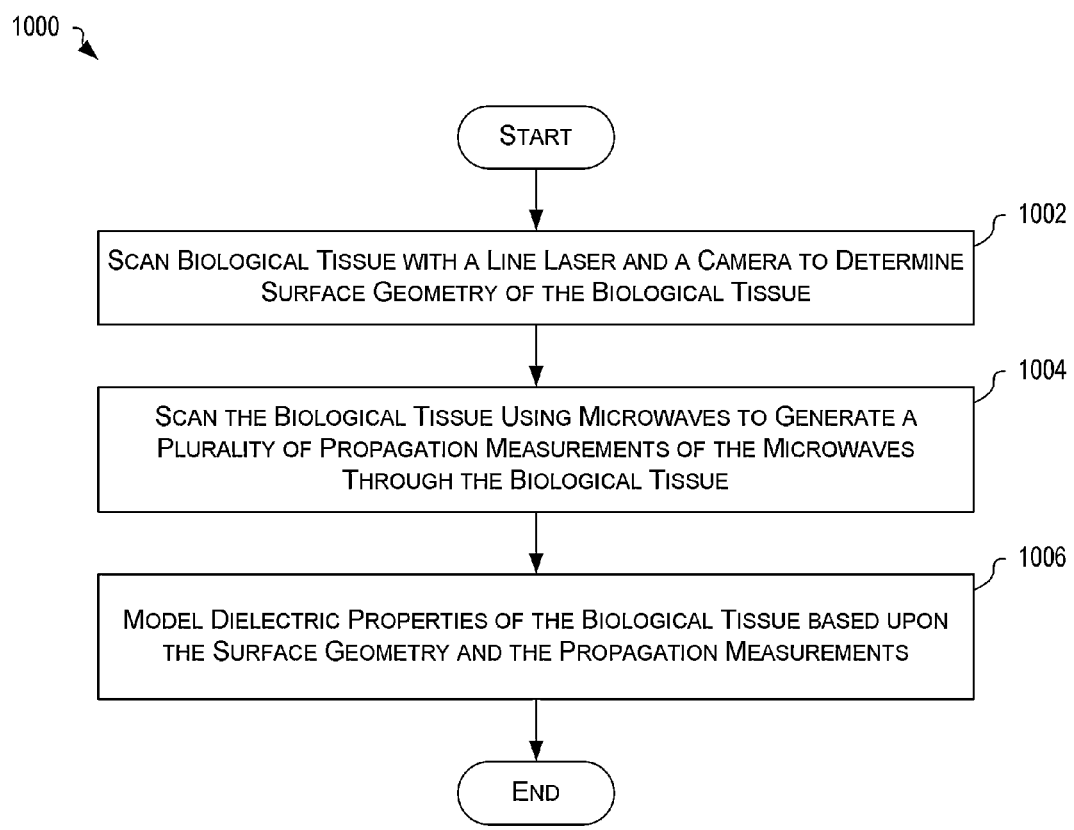
FIG. 10 is a flowchart illustrating one exemplary method for imaging biological tissue using microwave imaging system of FIG. 1 and the 3D laser scanning system of FIG. 2.

FIG. 10 is a flowchart illustrating one exemplary method 1000 for imaging biological tissue using a microwave-frequency RF signal and a 3D laser scanner. In step 1002, method 1000 scans the biological tissue with a line laser and a camera to determine surface geometry of the biological tissue. In one example of step 1002, system 200 determines 3D model 270 of surface geometry of object 202 immersed within tank 102. In step 1004, method 1000 scans the biological tissue using microwaves to generate a plurality of propagation measurements of the microwaves through the biological tissue. In one example of step 1004, system 100 utilized antennae 106 to scan object 202 immersed within tank 102. In step 1006, method 1000 models dielectric properties of the biological tissue based upon the surface geometry and the propagation measurements. In one example of step 1006, system electronics 120 of system 100 utilizes 3D model 270 and received signals indicative of microwave propagation through object 202 to model dielectric properties of object 202.

Various embodiments of the device include one or more of:

A system designated A for creating a 3D model of a surface of an object immersed in a transparent liquid within a stationary cylindrical transparent tank, comprising:

a rotating mount aligned to rotate around a central axis of the cylindrical transparent tank;

a camera fixedly attached to the rotating mount for capturing images of the object immersed in the transparent fluid;

a first laser projector fixedly attached to the rotating mount for projecting a first laser line perpendicular to a rotational plane of the rotating mount and aligned to the central axis, the first laser projector being positioned at a first angle relative to a field of view of the camera;

a second laser projector fixedly attached to the rotating mount to project a second laser line perpendicular to the rotational plane and aligned to the central axis, the second laser projector being positioned at a second angle relative to the field of view;

an actuator for rotating the rotating mount;

a controller for driving the actuator to rotate the rotating mount and to capture images from the camera at selected angular positions of the rotating mount; and an image processor further comprising an image correction function implemented as machine executable instructions within the image processor, the image correction function comprising a program selected from a ray tracing program and a registered image warping function, and a triangulation function determine, for each laser line within each image, a plurality of 3D positions where the laser line is incident upon a surface of the object.

In system designated B, the system designated A, further comprising a model generation program, implemented as machine executable instructions within the image processor, for generating a three-dimensional model of the surface of the object.

In a system designated C, the system designated A or B, further comprising a microwave imager that uses the 3D model of the surface of the object in reconstructing a three-dimensional model of dielectric properties within the object.

The system designated A or C, further comprising an optical encoder for determining the angular position of the rotating mount relative to an alignment position of the cylindrical transparent tank, the controller capturing the images based upon the output of the optical encoder.

The system designated A, wherein the image processor comprises a ray tracing program that calculates each of the 3D positions based upon the angular position of the rotating mount when the image was captured, intrinsic camera properties, the field of view, the first angle, the second angle, Snell's Law, and the refractive indexes of air, the transparent cylindrical tank, and the transparent liquid.

The system designated B, wherein the image processor generates a point cloud by combining the determined positions for each of the captured images.

In a system designated D, the system designated A, B, or C, wherein the first laser projector projects the first laser line in a first color and the second laser projector projects the second laser line in a second color that is different from the first color, and wherein the camera distinguishes the first laser line from the second laser line by color.

The system designated A or D, wherein the first laser line generator is positioned on a first side of the camera and the second laser line generator is positioned on an opposite side of the camera to the first side.

The system designated A, further comprising a calibration routine for generating calibration parameters, wherein the calibration parameters are used by the ray tracing program or image warping function to correct for refraction in determine the plurality of 3D positions.

A method designated M for generating a 3D model of a surface of an object immersed in a transparent liquid within a stationary cylindrical transparent tank, comprising the steps of:
  rotating a first and second laser line projectors and a camera around a central axis of the cylindrical tank, the first and second laser line projectors each generating a laser line perpendicular to a plane or rotation and aligned with the center of rotation, the camera imaging the object;
  capturing an image from the camera at each of a plurality of angular positions of the camera relative to a reference position of the stationary cylindrical tank;
  processing the captured images to determine, for each laser line within each image, a plurality of 3D positions where the laser line is incident upon a surface of the object; and
  generating a 3D model of the surface of the object based upon the plurality of 3D positions.

A method including the method designated M, further comprising the step of sensing the angular position of the camera relative to an alignment position of the tank and triggering the capture of the image from the camera based upon the angular position.

A method including the method designated M, wherein the step of processing comprises tracing, for each of a plurality of points identified on the laser lines within each of the captured images, a ray from the camera to the point of incidence of the laser line on the surface of the object based upon at least the refractive indexes of each of air, the transparent fluid, and the transparent cylindrical tank.

A method including the method designated M, further comprising the step of generating calibration parameters based upon images captured by the camera of a test grid positioned at the central axis, wherein the step of processing utilizes the calibration parameters to determine the plurality of 3D positions.

A method including the method designated M wherein the step of processing comprises performing a registered image warping function, the image warping function registered by a prior calibration procedure.

A system designated S for imaging biological tissue with a microwave-frequency RF signal, comprising:
  the system of claim A, B, C, or D for determining a surface geometry of the biological tissue within a cylindrical transparent tank;
  a plurality of antennas retractable from the cylindrical transparent tank, one or more of the plurality of antennas configured for receiving the microwave-frequency RF signal; and
  a signal processor coupled to the receiving antennas and configured for processing a demodulated signal representative of the microwave-frequency RF signal received by the one or more of the plurality of antennas to model the dielectric properties of the biological tissue based upon the surface geometry.

The system designated S, wherein the surface geometry is defined within a 3D model.

A method designated P for imaging biological tissue within a stationary cylindrical tank with a microwave-frequency RF signal, comprising the steps of:
  scanning the biological tissue with a line laser and a camera to generate a plurality of images;
  processing, within an image processor, the images to determine surface geometry of the biological tissue;
  scanning the biological tissue using microwaves to generate a plurality of propagation measurements of the microwaves through the biological tissue; and
  modeling dielectric properties of the biological tissue based upon the surface geometry and the propagation measurements.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:
1. A system for creating a 3D model of a surface of an object immersed in a transparent liquid within a stationary cylindrical transparent tank, comprising:
  a rotating mount aligned to rotate around a central axis of the cylindrical transparent tank;

a camera fixedly attached to the rotating mount outside the cylindrical transparent tank for capturing images of the object immersed in the transparent fluid;

a first laser line generator fixedly attached to the rotating mount outside the cylindrical transparent tank and configured to project a first laser line onto the object to simultaneously illuminate a plurality of points on the object, the first laser line being perpendicular to a rotational plane of the rotating mount and aligned to the central axis, the first laser line generator being positioned at a first angle relative to a field of view of the camera;

a second laser line generator fixedly attached to the rotating mount outside the cylindrical transparent tank to project a second laser line perpendicular to the rotational plane and aligned to the central axis, the second laser line generator being positioned at a second angle relative to the field of view;

an actuator for rotating the rotating mount;

a controller for driving the actuator to rotate the rotating mount and to capture the images at selected angular positions of the rotating mount; and an image processor comprising an image correction function implemented as machine executable instructions, the image correction function comprising (a) a registered image warping function configured to correct the images for refraction of light propagating from the first and second laser lines on the object through the transparent liquid, a wall of the cylindrical transparent tank, and air to the camera, and (b) a 3D coordinate function adapted to determine, from the images as corrected by the registered image warping function and for each laser line within each image, a plurality of 3D positions where the laser line is incident upon a surface of the object.

2. The system of claim 1, further comprising a model generation program, implemented as machine executable instructions within the image processor, for generating a 3D model of the surface of the object.

3. The system of claim 2, wherein the image processor generates a point cloud by combining the 3D positions, as determined by the 3D coordinate function, for each of the captured images.

4. The system of claim 2, further comprising a microwave imager that uses the 3D model of the surface of the object in reconstructing a three-dimensional model of dielectric properties within the object.

5. The system of claim 1, further comprising an optical encoder communicatively coupled with the actuator for determining angular position of the rotating mount relative to an alignment position of the cylindrical transparent tank throughout rotation of the rotating mount, the controller capturing the images based upon the output of the optical encoder.

6. The system of claim 1, wherein the first laser line generator and the second laser line generator are positioned on opposite sides of the camera.

7. The system of claim 1, further comprising a calibration routine for capturing calibration images by the camera and generating calibration parameters from the calibration images, wherein the calibration parameters are incorporated in the image warping function to correct for said refraction.

8. The system of claim 1, the first laser line generator being configured to project the first laser line in a first color and the second laser line generator being configured to project the second laser line in a second color that is different from the first color, and the camera being configured to distinguish points of the first laser line from points of the second laser line by color.

9. A method for generating a 3D model of a surface of an object immersed in a transparent liquid within a stationary cylindrical transparent tank, comprising the steps of:

rotating a rotating mount, coupled with a first laser line generator, a second laser line generator, and a camera around a central axis of the cylindrical transparent tank, each of the first laser line generator, the second laser line generator, and the camera being positioned outside the cylindrical transparent tank;

at a plurality of angular positions of the rotating mount:

(a) projecting a laser line from each of the first laser line generator and the second laser line generator onto the object such that each laser line simultaneously illuminates a plurality of points on the object, each laser line being perpendicular to rotational plane of the rotating mount and aligned to the central axis, and (b) using the camera, capturing an image of each laser line;

applying an image warping function to each image to correct the image for refraction of light propagating from the first and second laser lines on the object through the transparent liquid, a wall of the cylindrical transparent tank, and air to the camera;

processing each image, as corrected by the image warping function, to determine, for each laser line within each image, a plurality of 3D positions where the laser line is incident upon a surface of the object; and generating a 3D model of the surface of the object based upon the plurality of 3D positions determined for the plurality of angular positions.

10. The method of claim 9, further comprising:

sensing, using an optical encoder communicatively coupled with an actuator performing said rotating and throughout rotation of the rotating mount, angular position of the rotating mount relative to an alignment position of the cylindrical transparent tank; and triggering said capturing based upon said sensing.

11. The method of claim 9, further comprising:

generating calibration parameters based upon images captured by the camera of a test grid positioned at the central axis; and in the step of processing, utilizing the calibration parameters to determine the plurality of 3D positions.

12. The method of claim 9, further comprising:

in the step of projecting, using the first laser projector to produce a first laser line of a first color, and using the second laser projector to produce a second laser line of a second color different from the first color; and in the step of processing, distinguishing points of the first laser line from points of the second laser line by color.

13. A system for imaging biological tissue with a microwave-frequency RF signal, comprising:

a subsystem for determining a surface geometry of the biological tissue within a cylindrical transparent tank, the subsystem further comprising:

a rotating mount aligned to rotate around a central axis of the cylindrical transparent tank, a camera fixedly attached to the rotating mount outside the cylindrical transparent tank for capturing images of the biological tissue in the cylindrical transparent tank, at least one laser line generator each fixedly attached to the rotating mount outside the cylindrical transparent tank and configured to project a laser line onto the object to simultaneously illuminate a plurality of points on the object, the laser line generator being perpendicular to a rotational plane of the rotating mount and aligned to the central axis, each laser line generator being positioned at an angle relative to a field of view of the camera;

an actuator for rotating the rotating mount, a controller for driving the actuator to rotate the rotating mount and to capture the images at selected angular positions of the rotating mount, and an image processor comprising an image correction function implemented as machine executable instructions, the image correction function comprising:

(a) a registered image warping function configured to correct images for refraction of light propagating from each laser line on the object through the transparent liquid, a wall of the cylindrical transparent tank, and air to the camera, and (b) a 3D coordinate function adapted to determine, from the images as corrected by the registered image warping function and for each laser line within each image, a plurality of 3D positions where the laser line is incident upon a surface of the object;

a plurality of antennas retractable from the cylindrical transparent tank, one or more of the plurality of antennas configured for receiving the microwave-frequency RF signal; and a signal processor coupled to the receiving antennas and configured for processing a demodulated signal representative of the microwave-frequency RF signal received by the one or more of the plurality of antennas to model the dielectric properties of the biological tissue based upon the surface geometry determined by the subsystem.

14. The system of claim 13, wherein the surface geometry is defined within a 3D model.

15. The system of claim 13, the at least one laser line generator comprising:

a first laser line generator configured to produce a first laser line of a first color, and a second laser line generator configured to produce a second laser line of a second color different from the first color; and the image processor being configured to spatially distinguish points of the first laser line from points of the second laser line by color.

16. The system of claim 13, the signal processor being configured to utilize the surface geometry, as determined by the subsystem, to model the dielectric properties of the biological tissue by constructing a microwave model of dielectric properties constrained to have uniform dielectric properties external to the space defined by the surface geometry.

* * * * *

UNITED STATES PATENT AND TRADEMARK OFFICE
CERTIFICATE OF CORRECTION

PATENT NO. : 9,532,029 B2
APPLICATION NO. : 13/726050
DATED : December 27, 2016
INVENTOR(S) : Matthew Pallone et al.

It is certified that error appears in the above-identified patent and that said Letters Patent is hereby corrected as shown below:

In the Specification

At Column 1, Lines 17-20:
"The U.S. Government has certain rights in this invention as provided for by the terms provided by the National Institute of Health/National Cancer Institute for grant number PO1-CA080139."

Should read:
-- This invention was made with government support under grant numbers P01 CA080139 and R01 EB001982 awarded by the National Institutes of Health. The government has certain rights in the invention. --

Signed and Sealed this
Twenty-first Day of January, 2020

Andrei Iancu
*Director of the United States Patent and Trademark Office*